United States Patent
Pugsley, Jr. et al.

(10) Patent No.: US 9,247,939 B2
(45) Date of Patent: *Feb. 2, 2016

(54) METHODS AND DEVICES FOR MANIPULATING TISSUE

(71) Applicant: Boston Scientific Scimed, Inc., Maple Grove, MN (US)

(72) Inventors: Charles H. Pugsley, Jr., Pelham, NH (US); Barry N. Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/097,391

(22) Filed: Dec. 5, 2013

(65) Prior Publication Data

US 2014/0094832 A1    Apr. 3, 2014

Related U.S. Application Data

(63) Continuation of application No. 13/037,334, filed on Feb. 28, 2011, now Pat. No. 8,628,543, which is a continuation of application No. 10/992,232, filed on Nov. 19, 2004, now Pat. No. 7,918,864, which is a continuation of application No. 10/105,235, filed on Mar. 26, 2002, now Pat. No. 6,837,894, which is a continuation of application No. 09/432,575, filed on Nov. 12, 1999, now Pat. No. 6,387,104.

(51) Int. Cl.
*A61B 17/10*     (2006.01)
*A61B 17/064*    (2006.01)
(Continued)

(52) U.S. Cl.
CPC ........... *A61B 17/0644* (2013.01); *A61B 17/068* (2013.01); *A61F 5/0086* (2013.01); *A61B 17/0401* (2013.01); *A61B 2017/00818* (2013.01); *A61B 2017/00827* (2013.01); *A61B 2017/00867* (2013.01); *A61B 2017/0409* (2013.01); *A61B 2017/0417* (2013.01)

(58) Field of Classification Search
CPC ................. A61B 2017/00818; A61B 17/0401; A61B 17/0644; A61B 2017/0417; A61B 17/068; A61B 2017/0409; A61B 2017/00867; A61F 5/0086
USPC ......... 606/139, 151, 152, 153, 213, 215, 216, 606/217, 232, 129; 129/898
See application file for complete search history.

(56) References Cited

U.S. PATENT DOCUMENTS 3,276,448 A   10/1966  Kronenthal
3,874,388 A   4/1975   King et al.
(Continued)

FOREIGN PATENT DOCUMENTS

EP   0 464 480 A1   1/1992
EP   0 585 476      3/1994
(Continued)

*Primary Examiner* — Jing Ou
(74) *Attorney, Agent, or Firm* — Bookoff McAndrews, PLLC

(57) ABSTRACT

The present invention includes a method and apparatus for adhering tissue to one another. In an embodiment of the present invention the two tissues to be joined, for example the lower esophagus and the fundus of the stomach, are first placed adjacent to one another. Next a first restraint is placed near the outside surface of one of the tissues and a second restraint is placed near the outside surface of the other tissue. An irritant is then placed between the two adjacent tissues. The restraints, and consequently the tissue surfaces, are then drawn together. As the touching irritated tissue surfaces heal they will become bonded to one another and their need for the mechanical fastening of the restraints, to secure them together, will be diminished.

13 Claims, 7 Drawing Sheets

(51) Int. Cl.
     *A61B 17/068*   (2006.01)
     *A61F 5/00*     (2006.01)
     *A61B 17/00*        (2006.01)
     *A61B 17/04*        (2006.01)

(56) References Cited

U.S. PATENT DOCUMENTS

| | | | |
|---|---|---|---|
| 3,940,935 | A | 3/1976 | Richardson et al. |
| 4,016,721 | A | 4/1977 | Richardson et al. |
| 4,534,350 | A | 8/1985 | Golden et al. |
| 4,550,870 | A | 11/1985 | Krumme et al. |
| 4,669,473 | A | 6/1987 | Richards et al. |
| 4,750,492 | A | 6/1988 | Jacobs |
| 4,899,744 | A | 2/1990 | Fujitsuka et al. |
| 4,917,089 | A | 4/1990 | Sideris |
| 5,088,979 | A | 2/1992 | Filipi et al. |
| 5,108,420 | A | 4/1992 | Marks |
| 5,123,914 | A | 6/1992 | Cope |
| 5,192,301 | A | 3/1993 | Kamiya et al. |
| 5,203,864 | A | 4/1993 | Phillips |
| 5,269,809 | A | 12/1993 | Hayhurst et al. |
| 5,282,827 | A | 2/1994 | Kensey et al. |
| 5,284,488 | A | 2/1994 | Sideris |
| 5,382,231 | A | 1/1995 | Shlain |
| 5,403,326 | A | 4/1995 | Harrison et al. |
| 5,417,691 | A | 5/1995 | Hayhurst |
| 5,425,744 | A | 6/1995 | Fagan et al. |
| 5,433,727 | A | 7/1995 | Sideris |
| 5,451,235 | A | 9/1995 | Lock et al. |
| 5,470,337 | A | 11/1995 | Moss |
| 5,480,434 | A | 1/1996 | Eckstein et al. |
| 5,531,759 | A | 7/1996 | Kensey et al. |
| 5,558,665 | A | 9/1996 | Kieturakis |
| 5,571,116 | A | 11/1996 | Bolanos et al. |
| 5,634,936 | A | 6/1997 | Linden et al. |
| 5,676,674 | A | 10/1997 | Bolanos et al. |
| 5,700,277 | A | 12/1997 | Nash et al. |
| 5,709,707 | A | 1/1998 | Lock et al. |
| 5,741,297 | A | 4/1998 | Simon |
| 5,787,897 | A | 8/1998 | Kieturakis |
| 5,810,848 | A | 9/1998 | Hayhurst |
| 5,861,004 | A | 1/1999 | Kensey et al. |
| 5,887,594 | A | 3/1999 | LoCicero, III |
| 5,904,703 | A | 5/1999 | Gilson |
| 5,916,236 | A | 6/1999 | Muijs Van de Moer et al. |
| 6,045,497 | A | 4/2000 | Schweich, Jr. et al. |
| 6,080,182 | A | 6/2000 | Shaw et al. |
| 6,086,600 | A | 7/2000 | Kortenbach |
| 6,113,609 | A | 9/2000 | Adams |
| 6,156,044 | A | 12/2000 | Kammerer et al. |
| 6,206,907 | B1 * | 3/2001 | Marino et al. ............... 606/215 |
| 6,387,104 | B1 | 5/2002 | Pugsley, Jr. et al. |
| 6,494,888 | B1 | 12/2002 | Laufer et al. |
| 6,663,639 | B1 | 12/2003 | Laufer et al. |
| 8,057,494 | B2 | 11/2011 | Laufer et al. |
| 2004/0010245 | A1 | 1/2004 | Cerier et al. |
| 2005/0033328 | A1 | 2/2005 | Laufer et al. |
| 2009/0018558 | A1 | 1/2009 | Laufer et al. |

FOREIGN PATENT DOCUMENTS

| | | |
|---|---|---|
| SU | 1560134 | 4/1990 |
| WO | WO 88/09157 | 12/1988 |
| WO | WO 93/10714 | 6/1993 |
| WO | WO 99/22649 | 5/1999 |
| WO | WO 99/60931 | 12/1999 |
| WO | WO 00/57796 | 10/2000 |

* cited by examiner (PREVIOUSLY KNOWN)

METHODS AND DEVICES FOR MANIPULATING TISSUE

CROSS-REFERENCE TO RELATED APPLICATIONS

This application is a Continuation Application of U.S. patent application Ser. No. 13/037,334, filed Feb. 28, 2011, now U.S. Pat. No. 8,628,543, which is a Continuation Application of U.S. patent application Ser. No. 10/992,232, filed Nov. 19, 2004, now U.S. Pat. No. 7,918,864, which is a Continuation Application of U.S. patent application Ser. No. 10/105,235, filed Mar. 26, 2002, now U.S. Pat. No. 6,837,894, which is a Continuation Application of U.S. patent application Ser. No. 09/432,575, filed Nov. 12, 1999, now U.S. Pat. No. 6,387,104, all of which are incorporated herein by reference.

FIELD OF THE INVENTION

The present invention relates to the treatment of Gastro Esophageal Reflux Disease (GERD). More specifically the present invention provides a method and an apparatus for enhancing the function of the lower esophageal sphincter to preclude the occurrence of Gastro Esophageal Reflux Disease.

BACKGROUND OF THE INVENTION

Gastro Esophageal Reflux occurs when stomach acid splashes back through the lower esophageal sphincter into the esophagus. Highly acidic in nature, the stomach acid irritates the esophagus causing pain and discomfort. This discomfort manifests itself as heartburn, or in severe cases, as chest pains. A prolonged exposure to stomach acid will damage the esophagus and can contribute to other esophageal ailments such as Barrett's Esophagus.

Gastro Esophageal Reflux Disease, the repeated occurrence of gastro esophageal reflux, stems from an incompetent Lower Esophageal Sphincter (LES), one that has begun to inadequately close. No longer does the failing lower sphincter prevent stomach acid from splashing back into the esophagus as would a properly functioning lower sphincter. Instead, as digestion in the stomach progresses, the acid required to break down the stomach's contents refluxes, unrestricted by the lower esophageal sphincter, into the lower esophagus during each digestive cycle.

Both non-surgical and surgical methods of treatment are available to attempt to provide relief from the disease. Medications that diminish or even eliminate the acidic secretions in the stomach can be proscribed and administered to treat the sphincter dysfunction. While these medications may provide short term relief, they do not address the underlying problem of the malfunctioning sphincter. Surgery, another available treatment, seeks to address the underlying problem. One available surgical procedure, fundoplication, involves wrapping the fundus of the stomach around, and to, the lower esophageal sphincter in support of the sphincter. More specifically, as digestion begins to take place, gases begin to develop in the stomach. The amount and volume of gas increases as digestion progresses. Eventually, enough gas is present in the stomach to inflate and expand the fundus. Now wrapped around the esophagus, as the fundus inflates and expands it places pressure on the lower sphincter in support of the sphincter's complete closure. As the digestive cycle concludes the gases in the stomach subside and the closing pressure on the sphincter dissipates, once again allowing the sphincter to open.

Fundoplication has proven to be an effective method of treatment but not without some cost and risks. When the operation is performed, through an incision in the abdominal cavity (illustrated at 120 in FIG. 1), it is a significant one, often requiring one week of hospital stay and four to six weeks of additional recovery. Moreover, being performed in the abdominal cavity, the operation carries along with it the usual of abdominal surgery as well as the intraoperative risks associated with working near the esophagus and the cardia.

Other methods of performing a fundoplication are also known. For example, laproscopic procedures have been used to perform the operation. Here, rather than making an incision in the abdominal cavity, several surgical cannulas are inserted into the abdomen in various places. The surgery is then performed through these cannula portals by the surgeon as opposed to through a large incision in the abdominal cavity as would be utilized in a full abdominal fundoplication. Once completed, the recovery time from this process involves several days of hospital stay and a week or more of outpatient recovery time.

In another known approach, endoluminal procedures are used in conjunction with an abdominal incision to perform a fundoplication. Here, an invagination device containing several retractable needles is inserted into the mouth and down the esophagus to be used in conjunction with a manipulation and stapling device remotely inserted through an opening in the abdominal cavity. The fundoplication is performed by these devices with fasteners being employed to secure the fundus into its new position. In addition to requiring an abdominal breech, this procedure utilizes surgical staples that, due to the highly acidic nature of stomach acid, have not proven to be completely effective over time. Exposed to the stomach acid the staples can erode away thereby requiring a second identical procedure be performed. Other approaches also exist, but these too contain the same disadvantages—additional incisions, or mechanical fasteners susceptible to erosion from the stomach acid, or both.

It would, therefore, be desirable to have an apparatus and method for performing fundoplication wherein no additional incisions into the body would be required and wherein the risk of the fundus becoming dislodged due to the undermining of the integrity of the surgical fasteners would be diminished.

SUMMARY OF THE INVENTION

The present invention includes a method and apparatus for adhering tissue to one another. In an embodiment of the present invention the two tissues to be joined, for example the lower esophagus and the fundus of the stomach, are first placed adjacent to one another. Next, a first restraint is placed near the outside surface of one of the tissues and a second restraint is placed near the outside surface of the other tissue. An irritant is then placed between the two adjacent tissues. The restraints, and consequently the tissue surfaces, are then drawn together. As the touching irritated tissue surfaces heal they will become bonded to one another and their need for the mechanical fastening of the restraints, to secure them together, will be diminished.

DETAILED DESCRIPTION

Figure 1:
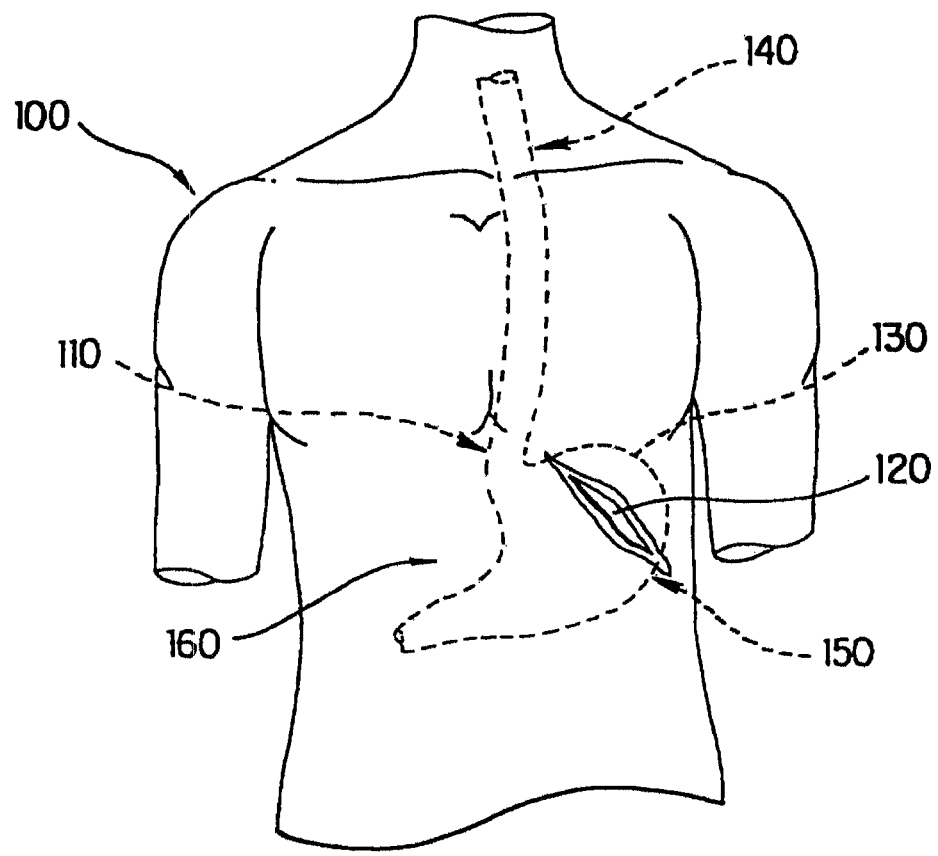
FIG. 1 illustrates a patient with an incision in the abdominal cavity as previously known.

The present apparatus and method can be used in the endoluminal treatment of Gastro Esophageal Reflux Disease. FIG. 1 illustrates a patient's body 100 with an upper esophagus 140, a lower esophagus 110, a stomach 150, and a fundus 130 as is previously known.

FIGS. 2A through 2F illustrate a pointed carrier 215 with anchors 205, 210, and 220 contained therein, as employed in an embodiment of the present invention. The pointed carrier 215 has a proximal end (not shown) and a distal pointed end 225. After securing the esophageal pathway, the pointed carrier 215, which may be 50 centimeters or more in length, is inserted, by the surgeon, into the patient's body 100, down the esophagus 140. The proximal end of the pointed carrier 215 (not shown) remains outside of the patient's body throughout the entire procedure for controlling and manipulating the pointed carrier. No incisions are required in performing the procedure as access into the esophagus is gained by the surgeon through the mouth (not shown). However, should a passageway through the mouth be unavailable, the pointed carrier can be inserted into the lower esophagus through several alternative surgical methods, including an incision in the trachea, as would be evident to those of skill in the art.

Figure 2A:
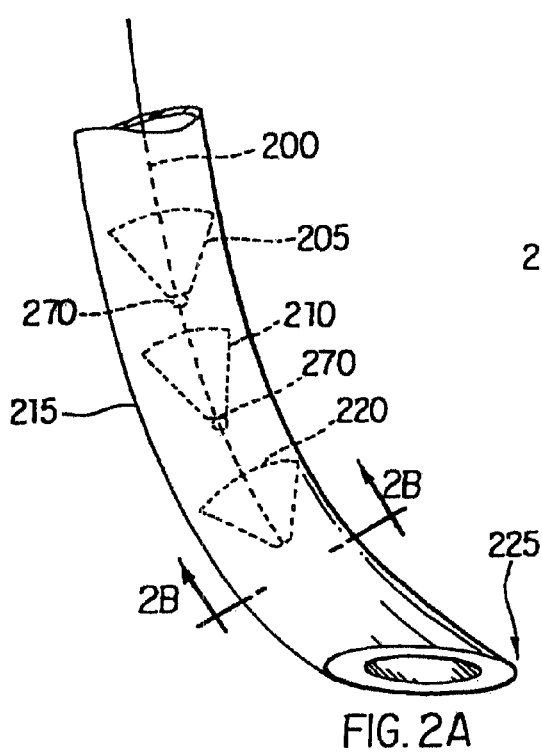
FIG. 2A illustrates the distal end of the pointed carrier in accordance with an embodiment of the present invention.

FIG. 2A illustrates the lower end of the pointed carrier 215 used in the present invention. The pointed carrier 215 terminates at a distal pointed end 225 sharp enough and strong enough to punch through the lower esophagus and the fundal wall of the stomach during the performance of the procedure. As is evident, the pointed carrier 215 is hollow and contains several surgical anchors or restraints. The first anchor 220, the second anchor 210, and the third anchor 205, are all located within the pointed carrier and are all impregnated with collagen to encourage tissue ingrowth and prompt recovery. The three anchors are also all affixed to a guy wire 200 which may be made from nitinol. These surgical anchors or restraints can vary in shape, size, and material. They can be circular, triangular, or any other shape and may be made from Meadox Mesh®, wire, genetically engineered tissue matched to the patient's tissue type or some other suitable material as will be apparent to one of skill in the art. The anchors should, however, have properties that allow them to fit inside the pointed carrier while remaining strong enough to grab, move, and support the organs and tissue in accordance with the steps described below.

The second anchor 210 and the third anchor 205 in FIG. 2A are slidably mounted on the guy wire 200. The first anchor 220 is permanently affixed to the distal end of the guy wire 200 by a securing button 260 (shown in FIG. 2B). This first anchor may rotate about the guy wire 200 but must be secured to it; able to withstand the pulling and anchoring forces placed upon it during the procedure. Knobs 270 are present on the guy wire to maintain spacing between each of the three anchors during the procedure. The knobs 270 are sized so that the second anchor 210 and the third anchor 205 maintain their spacing along the guy wire 200 during the procedure until they are pushed over the knob 270 and utilized within the body.

Figure 2B:
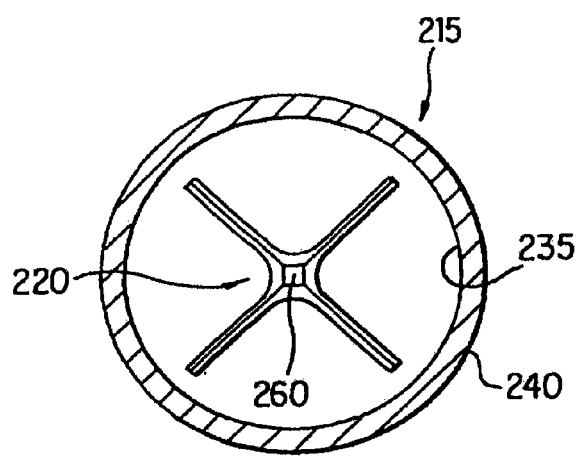
FIG. 2B illustrates a cross-sectional view as taken along line 2B-2B of FIG. 2A.

FIG. 2B is a cross-section as taken along line 2B-2B of FIG. 2A illustrating the leading tip of the first anchor 220 as loaded into the pointed carrier 215. FIG. 2B illustrates the outer surface 240 of the pointed carrier 215, the inner surface 235 of the pointed carrier 215, and button 260. Button 260 is attached to the distal tip of the guy wire 200 and firmly secures the first anchor 220 to the guy wire 200.

Figure 2C:
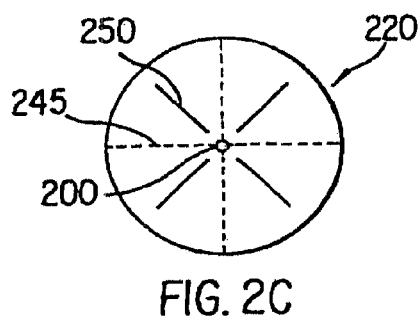
FIG. 2C illustrates an unfolded first anchor in accordance with an embodiment of the present invention.

FIG. 2C is an illustration of the first anchor 220 before it has been folded to fit into the pointed carrier 215. Nitinol wires 250 and the dashed fold lines 245 are clearly visible. Each anchor 220, 210, and 205 is folded in half and then in half again before they are loaded into the pointed carrier 215. The anchors and guy wire may be loaded by the surgeon before the procedure is to begin or they may be pre-loaded into the pointed carrier 215 by the manufacturer.

Figure 2D:
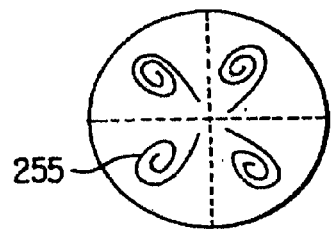
FIG. 2D illustrates an unfolded first anchor after it has entered the stomach in accordance with an embodiment of the present invention.

FIG. 2D is an illustration of anchor 220 after it has been deployed from the pointed carrier 215 into the body wherein the heat generated by the body has caused the previously straight nitinol wires 250 to bend into spiral patterns 255 having more rigid structural properties. Embedded into the first anchor 220 and the third anchor 205, these wires provide structural reinforcement for the anchors which must withstand severe forces both during the procedure and after they are secured in place.

Figure 2E:
FIG. 2E illustrates a nitinol wire before it has been exposed to the body heat of the patient in accordance with an embodiment of the present invention.

FIG. 2E illustrates the nitinol wire 250 before the anchor has been exposed to the patient's body heat.

Figure 2F:
FIG. 2F illustrates a nitinol wire after it has been exposed to the body heat of the patient in accordance with an embodiment of the present invention.

FIG. 2F illustrates the nitinol wire 250 in a spiral pattern 255 after the anchor has been exposed to the patient's body heat causing the wire to curl and become more rigid.

Figure 3:
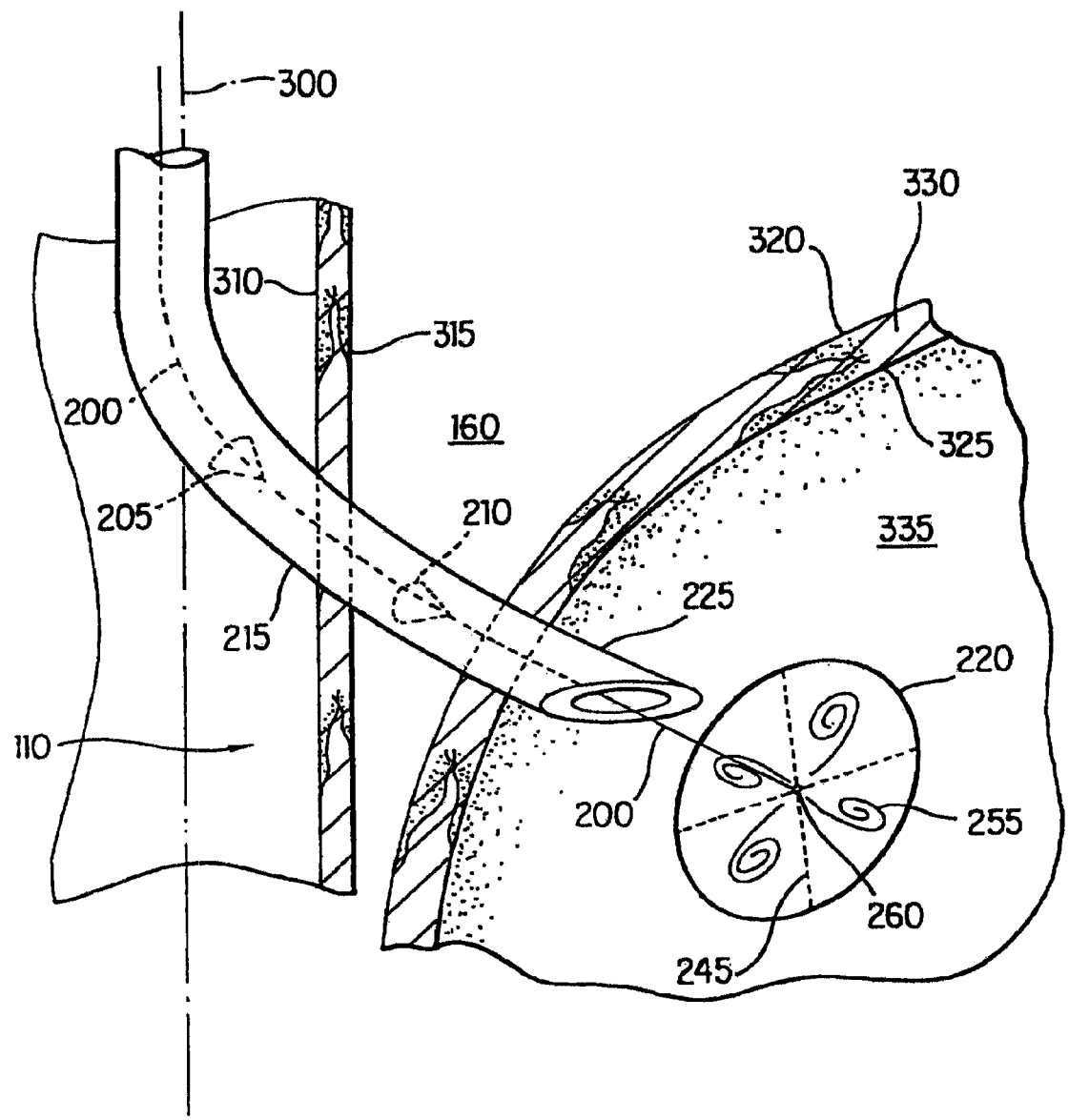
FIG. 3 illustrates the pointed carrier after it has punched through the lower esophageal wall and the fundal wall in accordance with an embodiment of the present invention.

A method of practicing the instant invention will now be further described. As is evident FIG. 3 illustrates the step of initially punching through the lower esophagus 110, the abdominal cavity 160 and the fundal wall 330, and into the stomach cavity 335. Carrying the three anchors, the pointed carrier 215 is positioned in the lower esophagus 110 by the surgeon from the pointed carrier's proximal end (not shown) using endoluminal visioning systems or other techniques known in the art. Then, having correctly positioned the pointed end 225, the surgeon forces or punches the carrier through the lower esophagus 110, through the abdominal cavity 160, through the fundal wall 330, ultimately coming to rest in the stomach cavity 335. After the pointed end 225 enters the stomach cavity 335, the first anchor 220 is deployed by manipulating the guy wire 200 at the proximal end of the pointed carrier 215, outside the patient's body 100. Once deployed, the first anchor 220 unfolds along the fold lines 245 to its original circular shape and the nitinol wires, now fully exposed to the body's temperature, coil into a spiral pattern 255 to add rigidity to the first anchor 220. The second anchor 210 and the third anchor 205 remain in the pointed carrier 215 for later deployment and use.

Figure 4:
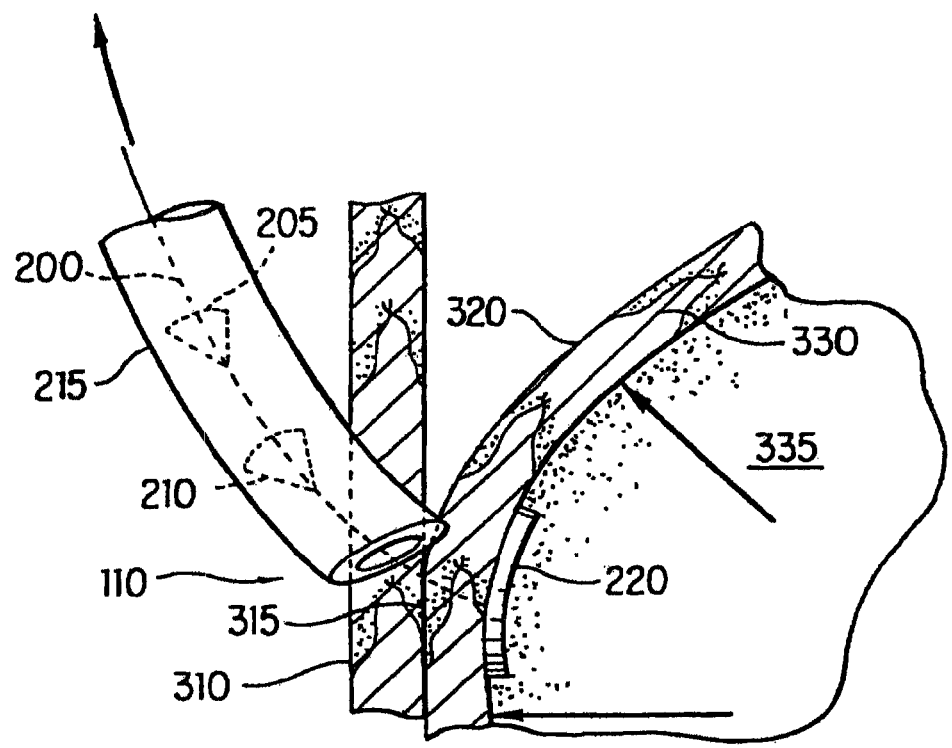
FIG. 4 illustrates an embodiment of the present invention wherein the fundal wall is being pulled against the lower esophagus.

As shown in FIG. 4, the pointed carrier 215 is then retracted back through the fundus into the lower esophagus. The first anchor 220, tethered to the guy wire 200, remains in the stomach cavity 335. The guy wire 200 is then reeled in, to first pull the first anchor 220 back, up against the inner wall of the fundus, and then to pull and lift the fundal wall 330 up against the outer wall of the esophagus 315. After the outer wall of the esophagus 315 and the outer wall 320 of the fundus 330 touch, the guy wire 200 is then released to allow the outer wall 320 of the fundus 330 to sag away from the outer wall 315 of the lower esophagus 110, thereby creating a void 500 (shown in FIG. 5) between the fundus 330 and the outer wall 315 of the lower esophagus 110.

After the fundus 330 sags back away from the lower esophageal wall 110, the pointed carrier 215 is pushed down, back through the lower esophageal wall 110, until the pointed tip is located in the void 500 between the outer fundal surface 320 and the outer wall 315 of the lower esophagus. As is evident from FIG. 5, the second anchor 210 is then deployed from the pointed carrier 215. It is deployed through the manipulation of the guy wire 200 at the proximal end of the pointed carrier 215 by the surgeon. Upon release from the pointed carrier, the second anchor 210, saturated with a sclerosing agent, and not containing any nitinol wires, unfolds. The second anchor does not need to contain the nitinol wires because it will not be exposed to the same level of force that will be placed upon the first and third anchors. The first and third anchors ultimately serve as restraints, compressing the fundal wall and the lower esophagus against each other. They, therefore, must be reinforced to withstand the uncompressing and expanding forces placed upon them in their final position. Conversely, the second anchor, which will ultimately be disposed between the other two anchors in its final position, will not be subjected to the same level of force and, consequently, does not require the nitinol wires be placed within it to reinforce it.

Figure 6:
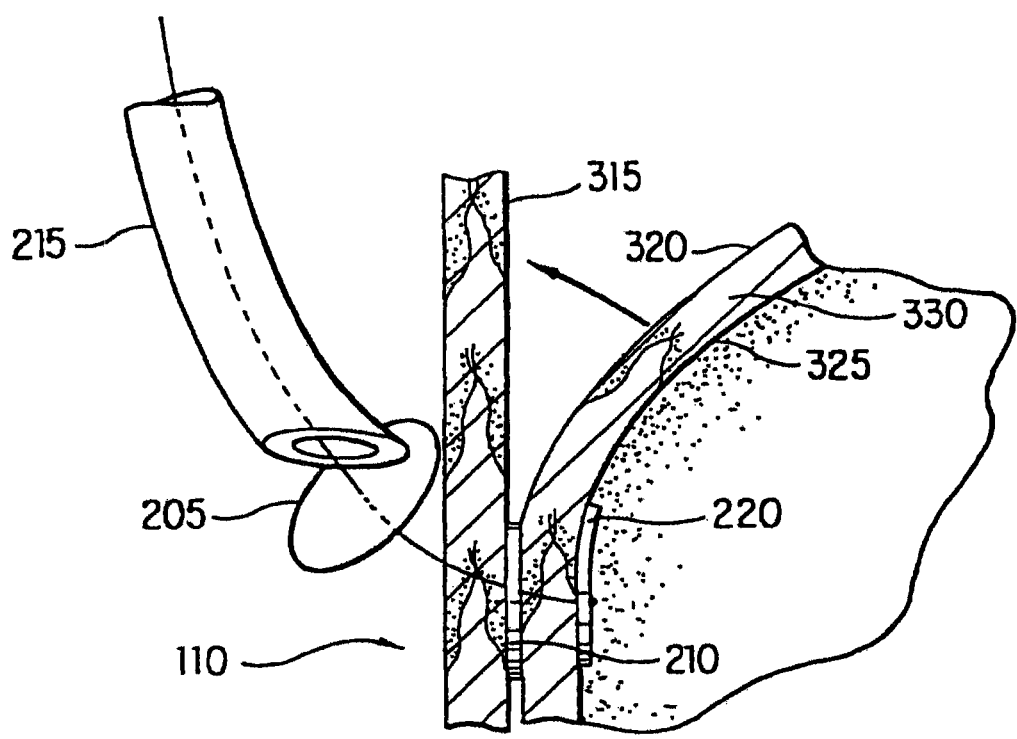
FIG. 6 illustrates an embodiment of the present invention wherein a third anchor has been deployed.

FIG. 6 illustrates the next step wherein the pointed carrier 215 is retracted back through the esophageal wall into the lower esophagus 110. The guy wire 200 is then reeled in, first bringing the first anchor 220 tight against the inner wall 325 of the fundus 330 and then bringing the second anchor 210 tight against the outer wall 320 of the fundus 330 and the outer wall 315 of the lower esophagus 110.

The second anchor 210, previously saturated with a sclerosing agent, now comes in contact with the outer wall 320 of the fundus 330 and the outer wall 315 of the lower esophagus 110, irritating both surfaces, the surrounding tissue, and the sclerosis of both the esophagus and the fundus (not shown).

The third anchor 205 is then deployed. Once deployed, the third anchor 205 is maneuvered to the inside wall of the lower esophagus to push and draw the esophageal wall and the fundal wall between the three anchors.

Figure 7:
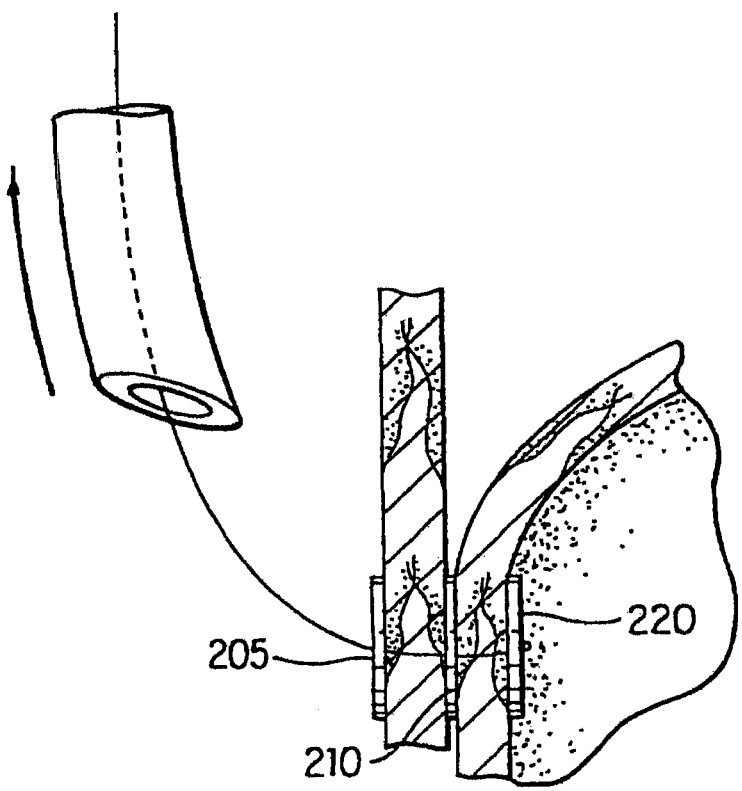
FIG. 7 illustrates an embodiment of the present invention wherein the pointed carrier is being removed from the esophagus.

FIG. 7 illustrates all three anchors after the third anchor has been placed parallel to the others, sandwiching the fundal wall and the esophageal wall. Once the anchors are drawn together, the pointed carrier is removed. The anchors are then locked in place by either crimping the wire, snapping a band over the wire or performing some other endoscopic procedure known to one of skill in the art. Once the anchors are locked in place the guy wire is cut and the unneeded portion is removed from the patient, once again through an endoscopic procedure known to one of skill in the art.

The three anchors are pulled tightly together, primarily to support the fundus, and secondarily to promote the bonding of tissue resulting from the irritant placed on the second anchor and the collagen impregnating all three anchors. The tissue irritated by the sclerosing agent and exposed to the collagen will promote tissue ingrowth between the stomach and the esophagus. Over time the nitinol guy wire and the anchors may dissipate leaving the ingrown tissues of the stomach and esophagus to be the sole bond between the esophagus and the fundus.

Alternatively, rather than impregnating all three anchors with collagen, the anchors may instead be made from genetically engineered tissue designed to match the tissue of the patient. These anchors, made from the genetically engineered tissue, like the collagen impregnated anchors, will promote the ingrowth and bonding of the fundus and the esophagus after deployment within the body.

Figure 8:
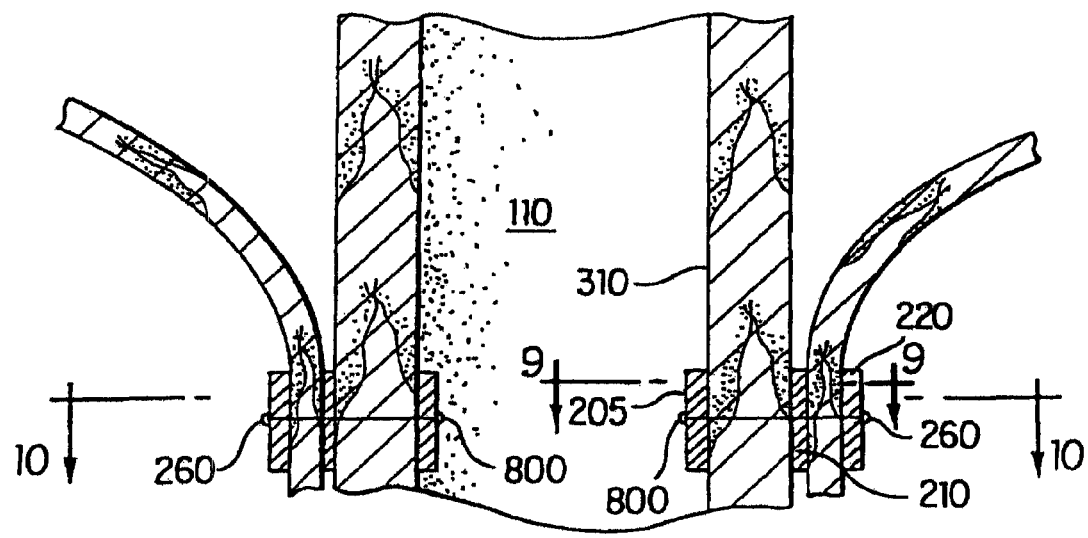
FIG. 8 illustrates the final position of anchors in accordance with an embodiment of the present invention.

FIG. 8 is an illustration of the first, second, and third anchors locked together after the method described above, an embodiment of the present invention, has been performed. As is evident, when the procedure is completed, the first and the third anchors border the fundus and the lower esophagus and serve as a support to hold them together. As is also evident, the knob 260 prevents the first anchor from slipping off the guy wire and the crimp 800, made by the surgeon during the procedure, prevents the third anchor from slipping off the guy wire.

Figure 9:
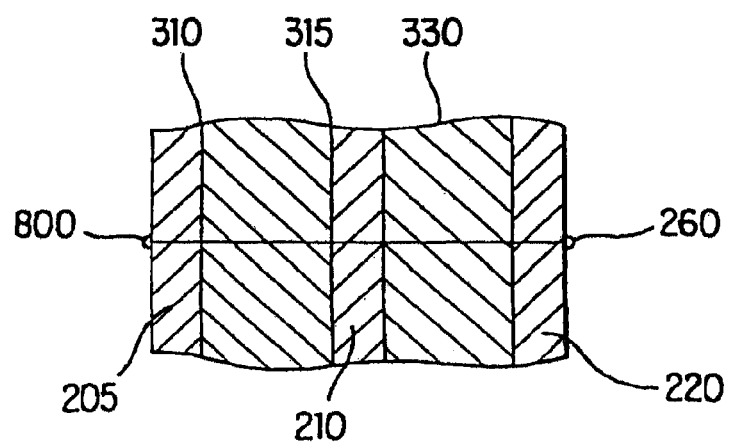
FIG. 9 illustrates a cross-sectional view as taken along line 9-9 of FIG. 8.

FIG. 9 is a cross-section as taken along line 9-9 of FIG. 8, illustrating the three anchors 205, 210, 220, the inner wall of the esophagus and the fundal wall 330 being sandwiched between the three anchors at the completion of the procedure. As will be recognized by one of skill in the art, the lower esophagus's circular cross-section requires that numerous anchors be placed in it to secure the fundus around the entire outer circumference of the lower esophagus. FIG. 9, therefore, illustrates an example of a single completed procedure, one of many that will be necessary to complete a full fundoplication. The actual number of anchors or restraints required varies depending on local conditions and remains within the discretion of the surgeon performing the procedure.

Figure 10:
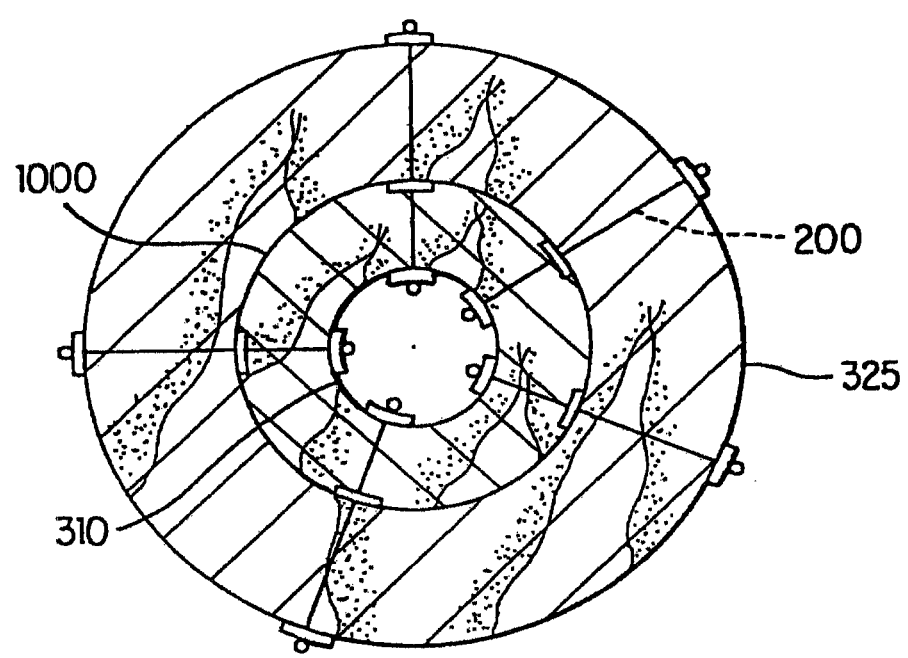
FIG. 10 illustrates a cross-sectional view as taken along line 10-10 of FIG. 8.

FIG. 10 is a cross-section, as taken along line 10-10 of FIG. 8, illustrating the esophagus and the fundus secured and positioned in accordance with an embodiment of the present invention. As is evident, multiple anchoring systems have been employed to properly secure the fundus to the lower esophagus.

Figure 5:
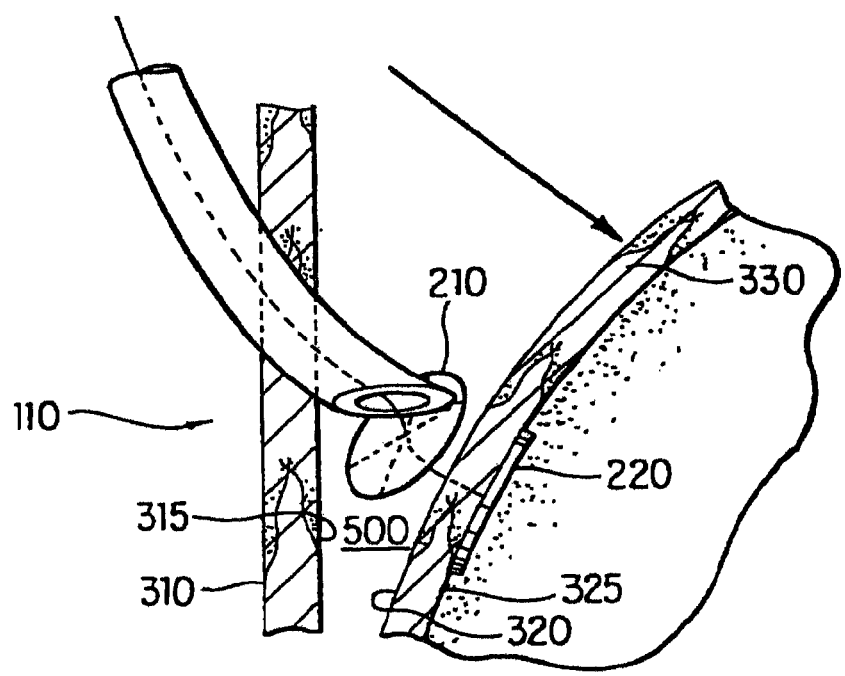
FIG. 5 illustrates an embodiment of the present invention wherein a second anchor has been deployed.

In another embodiment of the present invention, rather than using the second anchor to carry the irritating agent, the irritating agent can be squirted into place by the Endoscopist during the procedure. In this embodiment rather than having three anchors as shown in FIG. 2A only two anchors would be disposed along the guy wire 200 of FIG. 2A. After the fundus and the lower esophagus have touched rather than deploying the second anchor 210 as shown in FIG. 5, an irritant, such as a sclerosing agent, would be squirted down the pointed carrier 215 between the fundal wall and the esophageal wall to soak the surfaces of the organs that contact each other. Now bathed in irritant, the organs are then drawn together until they touch. Then the last anchor is deployed in the same manner as shown in FIG. 6 for the third anchor 205. The two anchors are then drawn together to pull the irritant soaked surfaces against one another. Once the soaked surface are pulled together the anchors are locked in place to maintain contact between the surfaces. As the irritated tissues heal the contacting surfaces will adhere to one another and the need for the surgical anchors, to hold them together, will be diminished.

As described above, a method and apparatus for curing Gastro Esophageal Reflux Disease is provided. The disclosed embodiments are illustrative of the various ways in which the present invention may be practiced. Other embodiments can be implemented by those of skill in the art without departing from the spirit and scope of the present invention.

What is claimed is:

1. A method of fastening two tissue portions, comprising:
    creating a fold of tissue including a first gastrointestinal tissue portion and a second gastrointestinal tissue portion;
    fastening the first gastrointestinal tissue portion to the second gastrointestinal tissue portion with a fastener, wherein the fastener includes a first anchor, a second anchor, and a connecting member for connecting the first and second anchors together, wherein the connecting member includes at least one spacer configured to maintain a spacing between the first and second anchors, wherein at least the second anchor is slidably connected to the connecting member, each of the first and second anchors is self-expanding, each of the first and second anchors includes a first material configured to promote tissue ingrowth, and each of the first and second anchors includes a heat-activated material including a nitinol wire configured to bend from a straight configuration to a spiral configuration at an elevated temperature; and
    expanding each of the first and second anchors from a contracted configuration to an expanded configuration upon exposure of the heat-activated material to the elevated temperature.

2. The method of claim 1, wherein each of the first and second anchors is formed of a second material, and the nitinol wire is embedded into the second material.

3. The method of claim 1, further including:
    inserting a pointed carrier containing the first anchor and the second anchor into a patient; and
    extending said pointed carrier through the first gastrointestinal tissue portion and the second gastrointestinal tissue portion.

4. The method of claim 3, wherein at least one of the first and second gastrointestinal tissue portions includes fundus tissue of a stomach.

5. The method of claim 3, wherein the pointed carrier comprises a hypotube.

6. The method of claim 1, wherein the first material configured to promote tissue ingrowth comprises collagen.

7. A method of fastening two tissue portions, comprising:
    creating a fold of tissue including a first gastrointestinal tissue portion and a second gastrointestinal tissue portion;
    fastening the first gastrointestinal tissue portion to the second gastrointestinal tissue portion with a fastener, wherein the fastener includes a first anchor, a second anchor, and a connecting member for connecting the first and second anchors together, wherein the first anchor is axially fixed to the distal end of the connecting member and the second anchor is slidably connected to the connecting member, each of the first and second anchors is self-expanding, each of the first and second anchors includes a first material configured to promote tissue ingrowth, and each of the first and second anchors includes a heat-activated material including a nitinol wire configured to bend from a straight configuration to a spiral configuration at an elevated temperature; and
    expanding each of the first and second anchors from a contracted configuration to an expanded configuration upon exposure of the heat-activated material to the elevated temperature.

8. The method of claim 7, wherein the connecting member includes a knob configured to maintain spacing between the first and second anchors.

9. The method of claim 7, wherein the first anchor is rotatable about the connecting member.

10. The method of claim 7, wherein each of the first and second anchors is formed of a second material, and the nitinol wire is embedded into the second material.

11. The method of claim 7, further including:
    inserting a pointed carrier containing the first anchor and the second anchor into a patient; and
    extending said pointed carrier through the first gastrointestinal tissue portion and the second gastrointestinal tissue portion.

12. The method of claim 11, wherein at least one of the first and second gastrointestinal tissue portions includes fundus tissue of a stomach.

13. A method of fastening two tissue portions, comprising:
    creating a fold of tissue including a first gastrointestinal tissue portion and a second gastrointestinal tissue portion;
    fastening the first gastrointestinal tissue portion to the second gastrointestinal tissue portion with a fastener, wherein the fastener includes a first anchor, a second anchor, and a connecting member for connecting the first and second anchors together, wherein the connecting member includes at least one spacer configured to maintain a spacing between the first and second anchors, wherein at least the second anchor is slidably connected to the connecting member, wherein at least one of the first and second anchors include a first material configured to promote tissue ingrowth, and each of the first and second anchors includes a heat-activated material including a nitinol wire configured to bend from a straight configuration to a spiral configuration at an elevated temperature, wherein each of the first and second anchors is formed of a second material, and the nitinol wire is embedded into the second material;
    expanding each of the first and second anchors from a contracted configuration to an expanded configuration upon exposure of the heat-activated material to the elevated temperature;
    inserting a pointed carrier containing the first anchor and the second anchor into a patient; and
    extending said pointed carrier through the first gastrointestinal tissue portion and the second gastrointestinal tissue portion.

* * * * *